United States Patent [19]

Spiess et al.

[11] Patent Number: 5,015,729
[45] Date of Patent: May 14, 1991

[54] OVINE INHIBIN

[75] Inventors: Joachim Spiess, Encinitas; Jean E. F. Rivier, La Jolla, both of Calif.; C. Wayne Bardin, New York City, N.Y.; Wylie W. Vale, Jr., La Jolla, Calif.

[73] Assignee: The Salk Institute for Biological Studies, San Diego, Calif.

[21] Appl. No.: 210,683

[22] Filed: Jun. 23, 1988

Related U.S. Application Data

[63] Continuation-in-part of Ser. No. 878,063, Jun. 24, 1986, abandoned, continuation-in-part of PCT US 87/01470 filed Jun. 23, 1987.

[51] Int. Cl.$^5$ ............................................. C07K 15/00
[52] U.S. Cl. ................................... 530/350; 530/387; 530/397; 530/398; 514/21
[58] Field of Search ............... 530/350, 324, 398, 397, 530/387; 435/68.1; 514/12, 21

[56] References Cited

U.S. PATENT DOCUMENTS

| | | | |
|---|---|---|---|
| 4,409,139 | 10/1983 | Ling et al. | 530/324 |
| 4,737,578 | 4/1988 | Evans et al. | 530/324 |
| 4,740,587 | 4/1958 | Ling et al. | 530/325 |

FOREIGN PATENT DOCUMENTS

| | | |
|---|---|---|
| 0222491 | 5/1987 | European Pat. Off. . |
| 86/00078 | 1/1986 | World Int. Prop. O. . |

OTHER PUBLICATIONS

Baker et al., "Studies on the Purification of Inhibin from Ovine Rete Testis Fluid," *Adv. Bioscience*, 82, pp. 123–132 (1982).
Baker et al., "Studies on the Purification of Ovine Inhibin," *Annals N.Y. Acad. Sci*, 383, pp. 329–341 (1982).
Al-Obaidi et al., "Suppression of Ovine Plasma FSH by Bovine Follicular Fluid: etc.," *J. Endocr.*, 111, pp. 1–5 (1986).
D. M. Robertson et al., "Isolation of Inhibin from Bovine Follicular Fluid," *B.B.R.C.*, 126, No. 1, pp. 220–226 (1985).
Chem. Abs., vol. 97, 1982, 66654a.
Chem. Abs., vol. 96, 1982, 211060g.
Chem. Abs., vol. 105, 1986, 165141w.

*Primary Examiner*—John Doll
*Assistant Examiner*—T. D. Wessendorf
*Attorney, Agent, or Firm*—Fitch, Even, Tabin & Flannery

[57] ABSTRACT

A dimeric protein with inhibin activity is isolated from ram reta testis fluid using reverse-phase high-performance liquid chromatography and gel filtration. The isolated molecule is composed of two chains having apparent molecular weights of about 18,000 and about 16,500 to 14,500 Daltons, as measured by gel electrophoresis, which are bound together by disulfide bonding and the longer of which is likely glycosylated. Microsequencing revealed the $NH_2$-terminal portion of the longer chain to be Ser- Thr-Pro-Pro-Leu-Pro-Trp-Pro-Trp-Ser-Pro-Ala-Ala-Leu-Arg-Leu-Gln-Arg-Pro-Pro-Glu-Glu-Pro-Ala-Ala-His-Ala-Asp-Cys and of the shorther chain to by Gly-Leu-Glu-Cys-Asp-Gly-Lys-Val-Asn-Ile-Cys-Cys-Lys-Lys-Gln-Phe. This dimeric protein specifically inhibits basal secretion of FSH, but not of LH, in a rat anterior pituitary monolayer culture system, exhibiting a half-maximal effective dose of about 0.1 to 0.3 ng/ml. Furthermore, antibodies raised against synthetic replicates of the N-terminal six residues of the longer chain, as well as against the N-terminal 25 residues, are effective to reduce the activity of highly purified intact ovine inhibin and might be used to exert a profertility effect in rams, ewes and other mammals.

4 Claims, 1 Drawing Sheet

Figure 1

OVINE INHIBIN

This invention was made with Government support under Contract NO1-HD-2-2824 of the National Institutes of Health. The Government has certain rights in this invention.

This application is a continuation-in-part of our earlier application Ser. No. 878,063, filed June 24, 1986, now abandoned and of International Application Ser. No. PCT/US87/01470, filed June 23, 1987.

The present invention relates to proteins having inhibin activity and more particularly to a protein first isolated to substantial homogeneity from material obtained from ovine animals.

BACKGROUND OF THE INVENTION

The existence of inhibin as a water-soluble substance of gonadal origin which acts specifically at the pituitary level to suppress the secretion of follicle-stimulating hormone (FSH) was postulated by McCullagh more than 50 years ago, *Science*, 76, 19-20 (1932). There has been great interest in it, and many laboratories have attempted to isolate and characterize such a substance.

The publications of a group working at the University of Melbourne in Australia (H. W. G. Baker et al., *Adv. Bioscience*, 1982, p. 123-132, and *Annals N.Y. Academy of Sciences*. 383 1982, pp. 329-342), reported on the disagreement between investigators as to the size of the inhibin molecule and as to what methods should be used for its attempted purification; moreover, the discussions reported at the end of these articles point out that there was even disagreement between investigators as to whether there was a hormone which fit the proposed definition of inhibin because bioassays that were being used in hopes of isolating such a substance were capable of measuring the activities of different substances that could have a similar effect. Thus, in 1982, investigators were generally admitting that methods for satisfactorily purifying a substance that appeared to have the activity of the proposed "inhibin" molecule had simply not yet been developed and, as a result, that the isolates that were then being obtained were still heterogeneous.

In *P.N.A.S.*, 82, 7217-7221 (November 1985), Ling et al. published the N-terminal sequences of a heterodimer of about 32 kD having inhibin activity that had been isolated from porcine follicular fluid. In *Nature*, 318, 659-663, (1985) Mason et al. published sequences for the subunits of porcine inhibin deduced from studies of cDNA, showing an α-chain of 134 residues linked to a β-chain of either 115 or 116 residues. In *B.B.R.C.*, 135, 3, 957-964 (Mar. 28, 1986), Mason et al. published sequences for the subunits of human inhibin similarly deduced from cDNA, also showing an α-chain of 134 residues linked to a β-chain of 115 or 116 residues. In May, 1986, in *P.N.A.S.*, 83, 3091-3095, Foragi et al. published sequences for subunits of bovine inhibin deduced from analysis of cDNA.

Inhibin may be used to regulate fertility, gonadotropin secretion or sex hormone production in mammalians, in females and particularly in males.

SUMMARY OF THE INVENTION

In accordance with the present invention, dimeric proteins having a molecular weight in the range of about 34,500 Daltons (34.5 kD) and 32,000 Daltons and having inhibin activity have been successfully isolated from ram rete testis fluid(RTF). Such proteins have been partially characterized using microsequencing methods.

Such proteins, isolated to substantial homogeneity from material obtained from RTF, are hereinafter referred to as ovine inhibin. These dimeric proteins are composed of two polypeptide chains having apparent molecular weights of about 18,000 Daltons and of between about 16,500 and about 14,500 Daltons, respectively, as measured by gel electrophoresis, the chains being linked together in the biologically active protein by disulfide bonding. The amino-terminal residue sequence of the larger 18 kD chain of the protein is Ser-Thr-Pro-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Ala-His-Ala-Asp-Cys-His-Arg-Ala. The amino-terminal sequence of the shorter chain is Gly-Leu-Glu-Cys-Asp-Gly-Lys-Val-Asn-Ile-Cys-Cys-Lys-Lys-Gln-Phe-Tyr-Val-Ser-Phe-Lys-Asp-Ile-Gly. The intact dimeric protein exhibits inhibin activity in that it specifically inhibits the basal secretion of FSH but does not inhibit basal secretion of luteinizing hormone (LH).

Purification of ovine inhibin to substantial homogeneity, i.e., about 90% to 98% by weight of total protein in the fraction, was achieved through a combination of protein separation procedures including gel filtration and reverse-phase, high-performance liquid chromatography (RP-HPLC).

DETAILED DESCRIPTION OF THE PREFERRED EMBODIMENTS

Using a multi-step procedure, the dimeric proteins were isolated to substantial homogeneity from ram rete testis fluid (RTF). The proteins are composed of two chains having apparent molecular weights of about 18 kD and about 16.5 kD to 14.5 kD, referred to respectively as the alpha subunit and the beta subunit, and the chains of the intact dimeric molecule are held together by disulfide bonding, the linkage between the chains being necessary for biological activity. Amino acid analysis of the total protein has been performed, and a partial amino acid residue sequence of each chain has also been determined, beginning at the amino-terminus. The chains are rich in Cys residues, and it is believed that internal disulfide bonding is also present. The amino-terminal sequence of the longer chain is Ser-Thr-Pro-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Ala-His-Ala -Asp-Cys-His-Arg-Ala. The 18 kD or α-chain is estimated to be about 135 residues in length, is likely glycosylated and is linked by one or more disulfide bridges to the β-chain. The shorter or β-chain has between about 115 and about 130 residues and probably has 115 or 116 residues; it begins at the N-terminus with the following sequence: Gly-Leu-Glu-Cys-Asp-Gly-Lys-Val-Asn-Ile-Cys-Cys-Lys-Lys-Gln-Phe-Tyr-Val-Ser-Phe-Lys-Asp-Ile-Gly. The C-terminus of either chain may be amidated or free acid.

The sharp elution peak of the protein which was obtained in the final chromatographic purification step is evidence that the protein has been purified to at least about 90% by weight of total protein. The 34.5 kD protein is water-soluble, and one of the subunits of the native protein is likely glycosylated. A second isolated molecule appears to have an N-shortened version of the α-chain, that is shorter by 15 residues, but is linked to an identical β-chain.

The intact protein exhibits inhibin activity in that it specifically inhibits basal secretion of FSH but not LH in a rat anterior pituitary monolayer culture system and exhibits a half-maximal effective dose ($EC_{50}$) of from about 0.1–0.3 ng/ml (3–10 pM.), based upon the assay described in detail in *Endocrinology*, 113, 1121-31 (1983). The isolated intact protein, as well as partially purified inhibin preparations, blocks the secretion of both LH and FSH in vitro when cells are stimulated by gonadotropin releasing hormone. In vivo, partially purified inhibin preparations are highly selective to decrease plasma FSH and not LH levels. The effects of inhibin on basal gonadotropin secretion in vitro appears to best reflect the in vivo situation. The intact dimeric protein is useful for regulating gonadotropin secretion and thus fertility and/or sex hormone production of both male and female mammalians. The possibility that RP-inhibin might have direct gonadal actions on gametogenesis or steroidogenesis is also likely, and some brain actions of inhibin are suggested.

A purification procedure was used to isolate ovine inhibin from crude RTF which utilized successive purification steps that include Reverse Phase-High Performance Liquid Chromatography (RP-HPLC) with different stationary phases and/or mobile phases and also include gel filtration or permeation Fast Protein Liquid Chromatography(FPLC).

The starting material for the procedure was about 3950 ml. of RTF that was first dialyzed against Milli Q $H_2O$ with 0.02% dimethylsulfide at 4C using dialysis bags with molecular weight cut off (MWCO) ca. 1000. The retentate was divided into two equal batches and lyophilized. Each half of the lyophilized pool was resuspended in column eluant and subjected to large scale gel permeation using a 5.0 by 150 cm glass column packed with 140 cm Sepharose CL-6B, $V_t$=2750 mls. Column eluant was 6 M Guanidine.HCl, 0.1 M ammonium acetate, 0.05% dimethylsulfide in Milli Q $H_2O$, ph 4.75. Eluant was 0.22 μm filtered and degassed before use. Flow rate was 50 mls/hour. Active fractions from the two batches were pooled and further processed.

Purification by semi-preparative RP-HPLC was carried out first at 50° C. and thereafter at room temperature (RT) using 133 ml-equivalents per run. The inhibin protein fractions from the various columns used for each step are pooled for each following step. Each run was applied directly onto a 1×30 cm Vydac 5-μm particle-size $C_4$ column (The Separations Group, Hesperia, Calif.) and eluted using a gradient of TEAP buffer. In this TEAP system, Buffer A consists of 0.1 N. triethylammonium phosphate(TEAP) pH 5, and Buffer B is 60% $CH_3CN$ in Buffer A. After all the filtrate had been loaded, the column was washed with the aqueous Buffer A until the UV absorption reached baseline. Flow through the column is maintained at 2.5 ml per minute. The column is loaded at 0% Buffer B, and a gradient for the mobile phase was then begun gradually changing to 95% over 30 minutes. The fractions are separated by an Altex 420 gradient liquid chromatography system equipped with a Spectroflow 773 UV detector (Kratos Analytical Instruments, Ramsey, N.J.) and a Servocoder SR 6253 strip chart recorder and are collected and tested for substantial inhibin activity.

Inhibin protein fractions from the various individual columns were pooled and further purified by a 1×30 cm Vydac 5-μm-particle-size $C_4$ column and a heptafluorobutyric acid (HFBA) buffer system at RT. In the HFBA system, Buffer A contains 1 ml of HFBA in 999 ml water, and Buffer B is 400 ml of water, 1 ml of HFBA and 599 ml of acetonitrile. Columns were loaded at 30% Buffer B followed by a gradient to 58% B in 25 minutes.

Active zones from reversed phase HPLC were lyophilized and resuspended in column eluant for processing on Pharmacia FPLC system by applying to two 1×30 cm Superose(FPLC) 12-B columns, 10 μm (Pharmacia Fine Chemicals, Piscataway, N.J.) linked in series. Each column was eluted with 6M guanidine.HCl, 0.1M ammonium acetate, pH 4.75, and 0.5% DMS in Milli Q $H_2O$ at a flow rate of 0.4 ml per minute for about 135 min. The column fractions were monitored by UV absorption and by bioassay. Active fractions eluted between $K_{AV}$=0.31–0.36.

Inhibin protein fractions from the various individual columns were pooled and further purified by RP-HPLC using 5-μm-particle-size $C_4$ column, 1×30 cm, and 0.5% $TFA/CH_3CN$ buffer system.

After such HPLC desalting, the active fraction was lyophilized and subjected to FPLC cation exchange by being brought up in Buffer A which was 50 mM sodium acetate, 4 M urea, 1 mM CHAPS (3-[(Cholamidopropyl) dimethylammonio]-1-propanesulfonate) in Milli Q $H_2O$, pH 5.3. Buffer B was 1 M NaCl in Buffer A. A Pharmacia FPLC system equipped with a Mono S HR 5/5 column, $V_t$=1 ml, was used at a flow rate of 1 ml per min. Column was loaded at 0% B followed by a gradient to 30% B in 25 minutes and then to 100% B in 5 minutes.

Next, the active fraction was applied to a 0.46×25 cm Vydac $C_8$ Column of reversed phase material with a 5 μm particle size and a 300A pore size. Buffer A is 0.1% (v/v) TFA in water and Buffer B is 1 ml TFA, 200 ml of water and 799 ml of acetonitrile. Flow rate was 0.7 ml/min at 40° C. with a back pressure of 900 psi. Buffer B was used at 25 volume % for the initial loading, followed by a gradient to 50% in 25 minutes. Two zones of active inhibin protein eluted, and both were separately processed thereafter.

Figure 1:
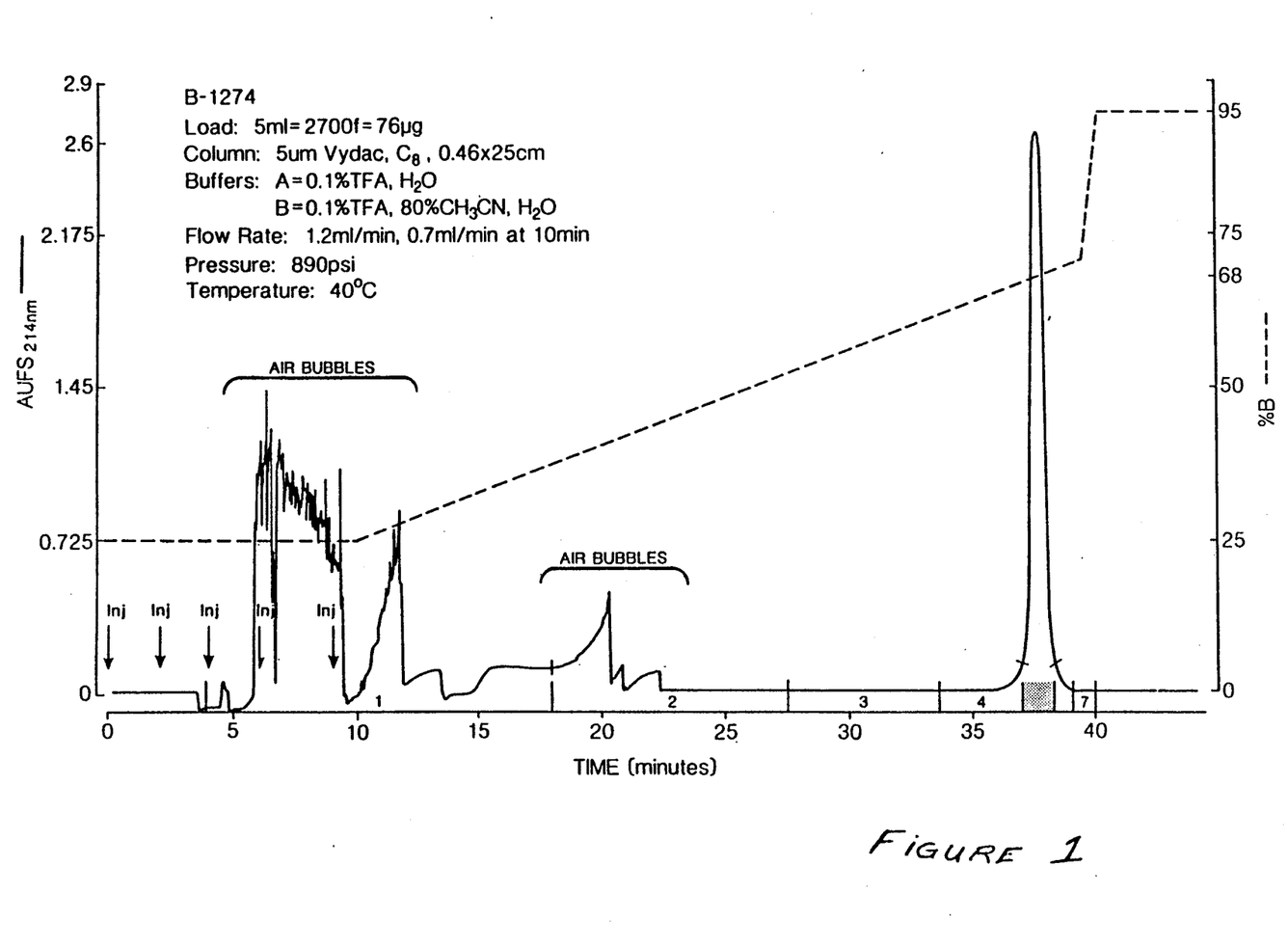
FIG. 1 is a chromatogram of the final RP-HPLC purification of an inhibin protein from RTF, active fractions of which were applied directly onto a 0.46×25 cm Vydac $C_8$ column with a 5 μm particle size and a 300A pore size, and eluted at 40° C. with a gradient of TFA/$CH_3CN$ buffers from 25% Buffer B to 95% Buffer B in 45 minutes, at a flow rate of 0.7 ml/min. with a back pressure of about 890 psi.

Each active fraction was applied to a 0.46×25 cm Vydac $C_8$ Column of reversed phase material with a 5 μm particle size and a 300A pore size. Buffer A is 0.1% (v/v) TFA in water, and Buffer B is 1 ml TFA, 200 ml of water and 799 ml of acetonitrile. Buffer B was used at 25 volume % for the initial loading at 40° C. and a flow rate of 1.2 ml/min. Then a gradient to 95% is run in 45 minutes at a flow rate of 0.7 ml/min at 40° C. with a back pressure of 890 psi, and a detector setting of 215 nm, 2.9 AUFS, which was slightly changed to 214 nm. before elution of the peak. The purified inhibin protein eluted generally between about 27.0 minutes and about 28.3 minutes after start of the gradient, which is equal to between about 18.9 ml and about 19.8 ml of elutant after start of the gradient. A chromatogram of the final step, for the later eluting active fraction from the previous step, is depicted in FIG. 1 and was generated using an Altex 420 System, two Beckman Model 100A pumps, a Datamark, Servocoder SR 6253 strip chart recorder, a Kratos, Spectroflow 773 variable wavelength, UV/visible detector and a Rheodyne 7125 injector with a 2.0 ml loop.

The inhibin protein fractions accumulated from all batches, respectively for the earlier and later eluting fractions, were pooled, resulting in a total of approximately 195 μg of inhibin protein, including about 120 μg of the earlier eluting active inhibin fraction and about 75 μg of the later eluting fraction. The 195 μg was estimated to have been obtained from about 2700 ml of RTF, with the remainder having been used in the biological testing that was carried out to identify the active fractions during purification.

Amino acid analyses of the substantially homogeneous, later eluting inhibin protein was performed after acid hydrolysis in 4M methane sulfonic acid and 0.2% tryptamine at 110° C. for 24 hours. Norleucine was used as an internal standard. The amino acid analyzer was a Beckman Model 121M with ninhydrin post-column derivatization. The results are shown in the Table below.

TABLE

AMINO ACID COMPOSITION OF PURIFIED INHIBIN PROTEIN FROM RAM RETE TESTIS FLUID

| Amino Acid | Inhibin Protein |
|---|---|
| Asx | 22 |
| Thr | 11 |
| Ser | 17 |
| Glx | 22 |
| Gly | 16 |
| Ala | 16 |
| Val | 11 |
| Met | 5 |
| Ile | 8 |
| Leu | 22 |
| Tyr | 8 |
| Phe | 10 |
| His | 8 |
| Trp | 4 |
| Lys | 10 |
| Arg | 10 |
| Cys | 12 |
| Pro | 23 |

Although the results of amino acid analysis of a large protein are not definitive of the precise composition because amino acid analysis can only provide a rough estimate, such results give a fairly accurate portrayal of relative residue compositions and together with other SDS and sequence data accurately define a pure compound.

A portion of the purified, later eluting fraction highest peak was exposed to 2% sodium dodecyl sulfate (SDS) with and without 5% β-mercaptoethanol at neutral pH in a boiling water bath for 2–3 minutes; both aliquots were subsequently applied to a slab gel and subjected to SDS polyacrylamide gel electrophoresis (PAGE) as described by Laemmli, U.K., *Nature*, 227, 680–685 (1970). Protein bands were discovered by silver staining.

On SDS-PAGE under non-reducing condition, the inhibin protein showed a single band migrating at about 34.5 kD. Under reducing condition, the inhibin protein separated into two bands, one migrating at about 18 kD and the other at about 16.5 kD or slightly below. Electrophoresis showed the protein was more than 90% pure.

Microsequencing, as described in Spiess, J. et al. *Biochemistry*, 20, 1982–1988 (1981), of the intact inhibin protein beginning at the NH$_2$-terminus consistently revealed two residues of approximately equal concentration at every cycle, indicating that the protein is composed of two chains. NH$_2$-terminal sequence analyses of the α- and β-chains of the dimeric inhibin protein were accomplished by first separating the two chains by SDS-PAGE under reducing conditions. Based upon the results from multiple sequencing analyses of both the intact and reduced inhibin protein, the sequence of the NH$_2$-terminal residues of the about 18 kD or alpha chain of the ovine inhibin protein is Ser-Thr-Pro-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Ala-His-Ala-Asp-Cys-His-Arg-Ala. The NH$_2$-terminal residues of the shorter or β-chain of the ovine inhibin protein are Gly-Leu-Glu-Cys-Asp-Gly-Lys-Val-Asn-Ile-Cys-Cys-Lys-Lys-Gln-Phe-Tyr-Val-Ser-Phe-Lys-Asp-Ile-Gly.

The remainder of the β-chain extending through the C-terminus is believed to be: Trp-Asn-Asp-Trp-Ile-Ile-Ala-Pro-Ser-Gly-Tyr-His-Ala-Asn-Tyr-Cys-Glu-Gly-Glu-Cys-Pro-Ser-His-Ile-Ala -Gly-Thr-Ser-Gly-Ser-Ser-Leu-Ser-Phe-His-Ser-Thr-Val-Ile-Asn-His-Tyr-Arg-Met-Arg-Gly-His-Ser-Pro-Phe-Ala-Asn-Leu-Lys-Ser-Cys-Cys-Val-Pro-Thr -Lys-Leu-Arg-Pro-Met-Ser-Met-Leu-Tyr-Tyr-Asp-Asp-Gly-Gln-Asn-Ile-Ile-Lys-Lys-Asp-Ile-Gln-Asn-Met-Ile-Val-Glu-Glu-Cys-Gly-Cys-Ser-OH. The β-chain also form a homodimer which counteracts the effect of inhibin, causing the release of FSH.

Once a substantial portion of the sequence of both chains of an inhibin protein is accurately known, the mRNA encoding the chains can be isolated, and the cDNA's can be synthesized by recombinant DNA techniques. Messenger RNA (mRNA) is obtained from ovarian follicules or from ram testes which produce inhibin, and then cDNA is synthesized from the mRNA by reverse transcription. The cDNA is inserted into a cloning vector which is used to transform a suitable host to create a cDNA library.

Based upon the known partial amino acid residue sequences of the inhibin chains, suitably labelled oligonucleotides are synthesized for detecting cDNA corresponding to each chain. Because of the degeneracy of the genetic code, mixed hybridization probes are prepared and used to select, from the library, cDNA clones that contain gene sequences encoding the chains. cDNA libraries may also be screened by immunological expression assay with an antibody raised either against inhibin or against one of the two inhibin chains. An immunological expression assay may also be used to confirm screening with hybridization probes.

From selected clones, cDNA is excised and inserted into appropriate vectors under the control of suitable promotor sequences, and the vectors are transformed into cell lines for expression of the recombinant inhibin chains. Although vectors containing the genes for both chains could be transformed into the same cell line, for simplicity, vectors for expression of each chain are preferably transformed separately into cell lines. The inhibin α- and β-chains can then be isolated from the cellular material and/or the cell culture medium. The two chains are then subjected to oxidizing conditions which promote disulfide bonding between the chains. Bonding between an α-chain and a β-chain produces an inhibin molecule, whereas bonding between two β-chains produces an FSH-releasing molecule. Moreover, a biologically effective inhibin molecule may be provided by bonding the α-chain to a β-chain having Phe instead of Tyr in the 17-position. The foregoing molecular biology techniques may also be used to read the gene sequences encoding the separate inhibin chains and thereby completely characterize the protein chains.

Substantially pure ovine inhibin or the nontoxic salts thereof, combined with a pharmaceutically acceptable carrier to form a pharmaceutical composition, may be administered to mammals, including humans, either intravenously, subcutaneously, percutaneously, intramuscularly or orally for control of fertility, gonadotropin secretion or sex hormone production.

Furthermore antibodies raised against synthetic fragments of inhibin, e.g. the six N-terminal residues of the α-chain, namely Ser-Thr-Pro-Pro-Leu-Pro, or the first 25 residues, neutralize the activity of purified inhibin. Thus passive (administration of antibodies) or active (administration of immunogenic inhibin as antigen) immunization methods could be employed to block endogenous inhibin and thereby elevate endogenous gonadotropin secretion and exert a profertility effect in sheep (both rams and ewes), in human beings and in other vertebrate animal species having inhibin of a similar polypeptide structure. The antibodies are also useful for achieving the efficient purification of inhibin by means of affinity chromatography via the creation of an immunoaffinity matrix.

Administration of inhibin induces decreased fertility in female mammals and decreases spermatogenesis in male mammals, and administration of a sufficient amount of inhibin could be employed to induce infertility in sheep, including rams and ewes, and in other mammals. Inhibin is also useful for tests to diagnose infertility.

In order to generate an antibody titer that is reactive with the inhibin protein so as to block its subsequent activity, synthetic conjugate molecules are produced which mimic the antigenic activity of inhibin, and the conjugate is exposed to a mammalian immune system, e.g., by inoculation into mammalian animals, for example rabbits or sheep, for the purpose of inducing the generation of antibodies reactive with the conjugate and also with the mimicked inhibin. The immune-response-inducing portion of the antigenic conjugate can be a synthetic peptide chain that is or contains a segment which is identical to or closely homologous to a segment of an inhibin protein chain. The portion of the inhibin chain to which the synthetic peptide segment is homologous should either be the active site of the inhibin protein chain or a site sufficiently close to the active site so that a bound antibody molecule inhibits hormonal activity of the inhibin protein, e.g., sterically. The twenty five residues of the N-terminus the α-chain will create antibodies that are very effective to inhibit the hormonal action of inhibin. The antigenic conjugate should also include a larger carrier moiety to which the synthetic peptide is linked, whereby the antigenic conjugate is sufficiently large to be recognized by the immune system of the inoculated animal, inducing its immune system to generate antibodies reactive with the conjugate.

Although inhibin itself is useful as an inoculum to induce the production of inhibin-reactive antibodies in a host animal, a synthetic antigenic conjugate which induces the production of antibodies that are also reactive with the endogenous inhibin molecule is preferred as inoculum. One major advantage of the use of a synthetic antigenic conjugate is the site-specificity which is achieved; whereas a synthetic inhibin antigen will only induce the production of antibodies reactive with the synthetic peptide chain and the mimicked portion of the inhibin molecule, the inhibin molecule induces the generation of antibodies reactive with a variety of antigenic determinants on the molecule. Accordingly, all inhibin-reactive antibodies that are induced by a conjugate containing a synthetic peptide and an appropriately selected mimicking peptide segment will neutralize inhibin, whereas some of the antibodies induced by natural inhibin protein may react with inhibin without neutralizing its hormonal activity. Because antibodies induced by an appropriate synthetic inhibin antigenic conjugate are all inhibin-deactivating, a lower titer may be administered to deactivate endogenous inhibin than a titer of antibodies that include antibody molecules which react with but do not inactivate or suppress hormonal activity. Minimizing the titer of inhibin-reactive antibody that is administered reduces the likelihood of inducing a significant immune response in the animal that is being treated.

Another important reason for avoiding the use of intact inhibin as inoculum for inducing the production of inhibin-reactive antibodies is that inhibin which is sufficiently pure to be used as inoculum is at this time very expensive. Moreover, because inhibin is therapeutically useful, expenditure of such a valuable material is desirably avoided.

It is well known to raise antibodies reactive with a proteinaceous material by synthesizing a short chain peptide corresponding to a portion of a protein chain of the material and linking the short chain synthetic peptide to a large carrier molecule so that the resulting peptide-carrier conjugate may be used as an antibody-inducing inoculum. Predictions have also been made as to which portions of a peptide chain would be expected to be immunogenically active; for example, it has often been suggested that peptide segments having a high proportion of hydrophillic amino acid residues can be expected to have a reasonable probability of being immunogenically active because such segments tend to align on the outside of the folded protein configuration in aqueous medium.

In practice, peptide-carrier conjugates have sometimes proven to be less suitable than desired for the purpose of inducing antibodies reactive with the endogenous protein. However, antibodies induced by synthetic antigenic conjugates utilizing the N-terminus of the 18 kD chain of the inhibin dimer not only react with the endogenous inhibins but finally inactivate the hormonal activities of inhibin. In assays using pituitary cell cultures in which inhibin protein is shown to inhibit secretion of FSH by the cells, the addition of (1) antibodies raised against the peptide-carrier conjugate plus (2) inhibin suppress inhibin activity and thus restores the level of secretion of FSH from the pituitary cell culture. The strong inactivating effect of such conjugate-induced antibodies on endogenous inhibins gives them sufficient potency to be administered to mammalian animals for the purpose of significantly depleting the availability of endogenous inhibin protein and thereby enabling increased amounts of FSH to be secreted by the pituitary.

The synthetic peptide is attached at its C-terminus, or at least downstream from the N-terminal residues, to the carrier molecule in order that the N-terminus of the synthetic peptide is outwardly exposed in the fashion of the N-terminus of the polypeptide chain of the natural inhibin molecule. To facilitate linking of the synthetic peptide to the carrier, the peptide may contain an amino acid residue at or closely adjacent to its C-terminus that can be linked by known linking chemicals to the carrier molecule, a C-terminal tyrosine (Tyr) being frequently used for this purpose. One or more additional amino acid residues, e.g. glycine (Gly), may be included intermediate within the synthetic peptide sequence to space the N-terminal mimicking sequence from the C-terminal peptide by which the peptide is linked to a carrier. The amino acid residue by which the peptide is linked to the carrier need not be the amino acid at the C-terminus of the synthetic peptide; however, adding additional amino acid residues at the C-terminus beyond the linking residue may be extraneous.

The carrier molecule functions to provide the conjugate with sufficient size so that the conjugate is recognized by the immune system of the animal into which the conjugate is inoculated. Generally, to be recognized, the carrier should have a molecular weight of at least about 10,000 Daltons and preferably at least about 60,000 Daltons. An important attribute of a carrier molecule is that it is itself not strongly inducing of immune responses in the animal that is inoculated for antibody-generating purposes, whereby the primary immune response induced by the conjugate is to generate antibodies reactive with the synthetic peptide. A suitable carrier molecule is alpha-immunoglobulin obtained from a mammalian species. Other suitable carrier molecules include, but are not limited to, keyhole limpet hemocyanin, mammalian serum albumin, e.g., bovine serum albumin, amino acid polymers, e.g., polylysine, polyarginine and amino acid copolymers, e.g., glutamic acid-lysine copolymer.

Unless the C-terminus of the synthetic peptide is chemically reactive directly with a functional group on the carrier molecule, a linking molecule (or molecules) is used to link the C-terminus of the synthetic peptide to the carrier molecule. Bisdiazotized benzidine (BDB) is commonly used to link a C-terminal tyrosine of a synthetic peptide to alpha immunoglobulin. BDB binds the tyrosine residue to tyrosine sidechains on the carrier protein molecule. Other linking chemical agents which may be used include glutaraldehyde for amino-to-amino coupling, water-soluble carbodiimides for carboxyl-to-amino coupling and maleimidobenzoyl-N-hydrosuccinimide ester for coupling cysteine sulfhydryls to amino groups. The choice of linking groups depends upon available side chains, and also selection is made so as not to alter the mimicking protein segment against which antibodies are to be raised. For example if the mimicking segment contains a tyrosine, a linking agent other than BDB may be selected.

The presence of tyrosine in the synthetic peptide also permits labeling of the completed peptide with radioactive iodine, e.g., $^{125}I$, by iodination of the tyrosine residue.

Synthesis of short peptide chains useful for producing synthetic inhibin antigen are known in the art and need not be described. Reference may be made to known protocols, such as W. Marki et al., *J. Am. Chem. Soc.* 103, 3178-2185 (1981). Peptides suitable for making synthetic inhibin antigenic conjugates may be less than ten amino acid residues long; however, the peptide containing the 25 N-terminal residues is known to be useful. The art of making synthetic peptides is sufficiently advanced that such relatively short peptides can be custom-ordered from certain biological supply houses, such as Bachem in Torrance, Calif. and Peninsula Laboratories in Belmont, Calif.

Inhibin-reactive antibodies and inhibin-mimicking antigenic substances are useful in immunoassay procedures for determining the level of endogenous inhibin in a mammalian fluid specimen. Inhibin-reactive antibodies and inhibin-mimicking substances can be used to determine the levels of endogenous inhibin in mammalian serum, abnormal inhibin levels being indicative of a hormonal cause of fertility problems. In determining the level of inhibin in mammalian fluid specimens, inhibin-mimicking substances compete with endogenous inhibin for binding sites upon inhibin-reactive antibodies. Either the synthetic peptides alone or the conjugates are useful in such competitive immunoassays; however, in immunoassays, non-conjugated synthetic peptides may be the preferred inhibin-mimicking substance.

Immunoassays include solution-phase and solid-phase, and competitive and non-competitive immunoassays and also include enzyme-linked immunosorbant assays and radioimmunoassays. Immunoassays are carried out by methods known in the immunoassay art for determining the concentration of a particular antigen (i.e., inhibin) in a specimen.

Should a competitive immunoassay be desired, one particular type of immunoassay suitable for inhibin is a competitive solid-phase assay wherein a quantity of inhibin-mimicking synthetic peptide and an unknown quantity of inhibin in a fluid specimen compete for binding by an inhibin-specific antibody. As a means of distinguishing and separating the known synthetic peptide and unknown inhibin quantities, either the peptide or the inhibin in the specimen is bound to a solid support (e.g., the inside wall of a microtiter plate well) while the other is maintained in solution. In the assay, an excess of the antibody is first incubated with and complexed with the entire amount of the support-bound substance, i.e. either the synthetic peptide or the inhibin; in a second step, the antibody remaining unbound is reacted with the other of the substances which is maintained in solution. In the first step, the complexing of antibody with one of the substances results in "inhibiting" antibody binding with the other substance in the second step.

The preferred of these competitive solid-phase immunoassays are ELISA's, such as that described by E. Engvall, et al., *Method Enzymol.*, 70: 419-439 (1980). Thus, the amount of antibody is measured which is not complexed in the first step but is complexed in the second, whether the amount is support-bound or in solution, after equilibrium has been reached. Measurement can be carried out by (1) reacting it with an antibody, preferably a polyclonal, subclass non-specific antibody, that reacts with immunoglobulin of the same class (e.g., $I_gG$) and from the same species (e.g., mouse or sheep) as the inhibin-reactive antibody and that has been previously linked to or complexed with an enzyme; (2) separating the portion of antibody-enzyme complex that binds to the earlier complex of antibody bound to inhibin or synthetic peptide from that portion which does not bind thereto; and (3) determining the amount of enzyme in either portion by exposing the same to a reagent or reagents which undergo a chromogenic reaction in the presence of the enzyme. The relative amounts of antibody binding to the known synthetic peptide and unknown inhibin quantities is a function of the unknown quantity of endogenous inhibin in the fluid specimen, and this quantity is determinable by comparison with a standard curve that is derived by assaying serial dilutions of known synthetic peptide or inhibin concentrations by the same procedure.

Radioimmunoassays represent another suitable technique whereby inhibin in an unknown specimen may be quantitated. For example, the labeling of the synthetic peptide might be with a radioisotope, such as $^{125}$I, e.g., through a tyrosine residue, rather than an enzyme, and the amount of labeled peptide measured (via radioactive emission). Iodination of a tyrosine residue of a synthetic peptide by the chloramine T method, purification of the iodinated synthetic peptide by cartridge extraction and HPLC, and use of the labeled synthetic peptide as a tracer in radioimmunoassay is described in Vale et al., "Neuroendocrine Peptides" *Methods in Enzymology*, Academic Press, New York (1983).

The generation of useful antisera directed toward the N-terminus of the inhibin 18 kD subunit is described hereinafter in greater detail by way of specific example.

EXAMPLE 1

The peptide ovine inhibin α(1-25)-Gly-Tyr having the formula H-Ser-Thr-Pro-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Gly-Tyr-OH is synthesized by the protocol described in W. Marki et al. (1981) supra. The first twenty-five amino acid residues correspond directly to the first twenty-five amino acid residues of the N-terminus of the alpha chain of 34.5 kD ovine inhibin. Tyrosine at the C-terminus serves as the means by which the peptide is conjugated to immunoglobulin, and glycine at the next position spaces the inhibin-mimicking sequence from the tyrosine residue. The synthetic peptide is made using the Merrifield synthesis and purified on HPLC according to the method of J. Rivier et al., *J. Chrom*. 288, 303-328 (1984). Amino acid composition gives the expected ratios. The purity of the peptide OIN(alpha)(1-25)-Gly-Tyr is greater than 98% as determined by analytical HPLC.

The synthetic peptide is coupled to human alpha-immunoglobulin through BDB, generally as described previously by W. Vale et al., *Methods in Enzymology* "Neuroendocrine Peptides", pp 565-577 Academic Press, N.Y. (1983). The reaction is halted by dialysis against 0.9% NaCl using dialysis tubing with a molecular weight cutoff of 1000. Through this process approximately 50 of the synthetic peptide moieties are bound to each immunoglobulin moiety.

Tracers are prepared with the synthetic fragments of ovine inhibin using Na$^{125}$I and the Chloramine T method. The molar ratio of synthetic peptide:Na$^{125}$I:Chloramine T is 1:1:10. Tracers are purified using high-performance liquid chromatography (HPLC) with a 0.1% TFA/acetonitrile solvent system.

To raise antibodies, rabbits are inoculated initially with intravenous injections of 1.0 mg of conjugate in 1 ml. of equal volumes of saline and Freund's complete adjuvant and every two weeks thereafter with 0.5 mg. One week following the third inoculation, bleedings are made, and the serum is saved. Antiserum from each rabbit is characterized with respect to titer and affinity for the tracer. The antibody titer (Ab$_1$) that is used for immunoneutralization binds 21% of the labeled peptide at 1:3000 final dilution.

A radioimmunoassay of inhibin α-chain is carried out using chilled reagents and with tubes partially immersed in ice water. On day one, 100 μl of buffer with antibody at the proper dilution is added to borosilicate glass tubes containing standard or test samples or buffer only in a volume of 300 μl. All treatments are tested in duplicate. Standards ranging from 1 to 10,000 pg of synthetic peptide fragment are used. Samples are generally tested at 2-5 dose levels, and standard curves are included at the beginning and the end of the assays. After these additions, tubes are vortexed and maintained at 4° C. for approximately 24 hours.

On day two, 20,000 cpm of $^{125}$I-labelled tracer with 0.5% normal rabbit serum (as carrier) is added in a volume of 100 μl to all tubes. The tubes are vortexed and returned to 4° C. for approximately 24 hours.

On day three, tracer bound to antibody is precipitated with sheep anti-rabbit gamma globulins and 10% PEG. To all tubes, except "total counts" tubes, 100 μl of sheep anti-rabbit gamma globulins at proper dilution (generally 1/40) and 0.5 ml of 10% PEG are added. The tubes are vortexed and incubated for 15 to 30 minutes at room temperature. All tubes, except "total counts" tubes, are washed with 1 ml wash buffer and centrifuged at 4° C. for 30-45 minutes at 2000×g. Supernatants which contain tracer not bound to antibody are decanted, and the pellets are counted in a gamma counter. Results are calculated using the logit/log radioimmunoassay data processing program of Faden, Huston, Munson and Rodbard (NICHD RRB, NIH).

For rat plasma samples, the radioimmunoassay uses an antibody at 1/325,000 final dilution with ovine inhibin α(1-25)-Gly-$^{125}$I-Tyr as a tracer and ovine inhibin α(1-25)-Gly-Try as a standard. The EC$_{50}$ and minimal detectable amounts for the synthetic peptide standard are about 27 pg and about 1-5 pg per dose respectively.

Antisera to inhibin α-chains can be affinity purified using the synthetic fragments, for preparation of immunoaffinity columns and for use in Western Blot analysis and immunocytochemistry. It is also desirable to purify antibody titers prior to administration to animals for control of fertility. The synthetic peptides which are used for forming the antigenic conjugates may also be used as a basis for antibody purification by affinity chromatography. The synthetic peptides are linked to conventional solid support material and the support material then packed as chromatography columns. Antisera is exposed to the column under conditions which allow antibody molecules to bind with the synthetic peptide moieties, and then the column is washed with solution that releases the antibodies from the column. Western blots and immunocytochemistry using such affinity-purified antisera have much reduced background, and immunoaffinity columns prepared using purified antiserum give superior results to those made using the total IgG fraction of serum.

Antiserum produced in rabbits is purified using an affinity column to which ovine inhibin α(1-25)-Gly-Tyr is covalently attached. Affi-Gel 10(BioRad), a cross-linked agarose gel with a 10 atom neutral spacer arm and active N-hydroxysuccinimide ester, is used for coupling with 100 mM NaHEPES (CalBiochem), pH 7.5 as coupling buffer. Ovine inhibin α(1-25)-Gly-Tyr (10 mg, about 2.3 moles) is dissolved in 1 ml H$_2$O and further diluted to 20 mls in coupling buffer. Affi-Gel 10 (15 mls bed volume) is transferred to a sintered glass funnel and washed with ice cold H$_2$O. The Affi-Gel 10 is mixed with the synthetic peptide and allowed to rotate for 4 hours at 4° C. using a Roto-Torque rotator (Cole-Parmer). The gel is spun down, and supernatant containing uncoupled ovine inhibin α(1-25)-Gly-Tyr is removed. The remaining active ester is blocked by the addition of 15 ml 1 M ethanolamine-Cl, pH 8, followed by rotation at 4° C. for 1 hour. The gel is spun down, and supernatant is removed. Noncovalently bound peptide is stripped from the gel by Washing with 20 column Volumes (300 ml) of 1 N acetic acid. Affi-Gel 10-ovine inhibin α(1-25)-Gly-Tyr is then equilibrated with 200 ml of 50 mMolar NaHEPES, pH 7.5. Coupling efficiency of ovine inhibin α(1-25)-Gly-Tyr to Affi-Gel 10 is about 90%.

About 40 mls of antiserum (40 nmoles binding sites per ml antiserum) is rotated overnight with Affi-Gel 10-ovine inhibin α(1-25)-Gly-Tyr at 4° C. Antiserum and gel are then packed into a 1.5×10 cm column (Bi-oRad) at 30 mls/hour. The column is washed extensively with 50 mM NaHEPES containing 1 mM CHAPS, pH 7.5, at 30 mls/hour to remove nonspecifically bound material. Specific immunoglobulins to ovine inhibin α(1-25)-Gly-Tyr are then eluted using 1 N acetic acid. The purified immunoglobulin fraction is neutralized and dialyzed against 150 mM NaCl, 50 mM NaHEPES, 0.05% NaAzide, pH 7.5. at 4° C. with three buffer changes using Spectrapor (Spectrum Medical) dialysis tubing with molecular weight cutoff 12,000 to 14,000.

The affinity-purified antiserum (45 ml equivalents=73 mg total protein) is coupled to 25 ml bed volume of Affi-Gel 10. The Affi-Gel 10 is washed with distilled $H_2O$ and the antiserum in 150 mM NaCl, 50 mM NaHEPES, 0.05% NaAzide, pH 7.5, is added. The gel is allowed to rotate with antiserum for 24 hours at 4° C. using Roto-Torque (Cole-Parmer). The gel is spun down, and the supernatant containing uncoupled antiserum is removed. Remaining active ester is blocked by the addition of 25 mls of 1 M ethanolamine-Cl, pH 8.0, and the gel is again rotated for one hour at 4° C. The gel is spun down, and the supernatant is removed. The gel is stripped of noncovalently bound antibody by successive washes with:

(1) two bed volumes $H_2O$
(2) two bed volumes 2 M guanidine thiocyanate
(3) two bed volumes $H_2O$
(4) two times two bed volumes 1 N acetic acid.

For each wash, the gel slurry is rotated at 4° C. for 30 minutes. The gel is then spun down, and the supernatant is removed. The gel containing covalently bound antiserum is equilibrated with 100 mM NaHEPES, pH 7.5. Approximately 70%-80% of the affinity-purified antibody is covalently coupled to the Affi-Gel 10, and it is ready for use in the affinity chromotography purification of inhibin.

Rete testis fluid (RTF) from adult rams is collected and averages 700 μg protein per milliliter; it possesses inhibin-like bioactivity and immunoactivity. Throughout the purification, fractions are monitored for inhibin activity using either or both the in vitro bioassay or the radioimmunoassay. Batches of RTF purified by immunoaffinity chromatography are screened by RIA using ovine inhibin α(1-25)-Gly-Tyr as a standard.

For the immunoaffinity columns and reverse phase HPLC columns, aliquots for assays (0.01-1.0% of the total fraction volume but never less than 5 μl) are transferred into polypropylene tubes containing bovine serum albumin (10 μl of 10 mg/ml) and dried in a Speed-Vac (Savant). For FPLC gel permeation columns where desalting is necessary before assay, small aliquots are removed and transferred to glass tubes containing 0.5 ml of 10 mM sodium HEPES+0.1% bovine serum albumin, pH 7.5. Squares of dialysis tubing with a molecular weight cutoff of about 1000 are secured over the tops of the glass tubes with rubber bands. The covered tubes are inverted and dialysed against 10 mM NaHEPES, pH 7.5. The retentates are then dried using a Savant Speed-Vac. All fractions are resuspended in cell culture medium for the in vitro bioassay or in RIA buffer for the radioimmunoassay.

Ram RTF, 2000 mls per batch, is processed using the affinity-purified antibody-Affi-Gel 10. For each batch, the RTF is allowed to rotate with the immunoaffinity matrix for 48 hours at 4° C. The mixture is then packed into a 1.5×10 cm column at 25 ml/hour. The column is then washed at 30 ml/hour with 1 mM CHAPS in 100 mM $NaPO_4$ buffer, pH 7.4. Proteins specifically bound to the immunoaffinity matrix are then eluted using 1 N acetic acid at a flow rate of 30 ml/hour. For the immunoaffinity chromatography, recovery of immunoactivity is 85% and recovery of bioactivity is 40%. This difference is due to material not retained by the column which contains bioactivity but not immunoreactivity using this N-terminally directed antibody when not reduced. Western Blot analysis shows only material with α-chains of about 19,000 to 21,000 and about 44,000 is retained by the immunoaffinity column. Unretained material has truncated αchains.

The active fraction from the immunoaffinity column is pooled, lyophilized, resuspended in gel filtration column eluant, and further purified using an FPLC system (Pharmacia) equipped with tandem Superose 12B columns, 10 μm, 10×300 mm each. The column eluant is 6 M Guanidine-HCl, 0.1 M ammonium acetate, pH 4.75; the flow rate is 0.4 ml/min. Fractions are collected every 1 min. The active fraction from immunoaffinity column is generally processed in two batches of not more than 5 mg total protein per run to optimize resolution. Two zones of immunoactivity are eluted, but only the later eluting zone is biologically active. The two active zones from the FPLC gel filtration are separately purified using a Beckman HPLC system with reverse phase columns. The zone with both immunoactivity and bioactivity is purified in three batches using a Vydac C8 column, 0.46×25 cm, 5 μm particle size, at 40° C. Buffer A is 0.1% trifluoroacetic acid (TFA); buffer B is 80% acetonitrile in 0.1% TFA. Columns are loaded at 25% B at a flow rate of 1.2 ml/min and then a gradient is run to 95% B in 45 minutes at a flow rate of 0.7 ml/min. The active zone from the three runs is pooled and then concentrated using a gradient of 25% B to 95% B in 70 minutes at a flow rate of 0.7 ml/min. The active fraction from this column is analyzed for purity using SDS polyacrylamide gel electrophoresis, for composition using Western Blot analysis, and is also sequenced.

Analysis of the highly purified fraction with both immunoactivity and bioactivity by SDS-PAGE using a gradient of 8-25% acrylamide shows a single band of about 32,000 Daltons unreduced, and bands of about 21 kD and about 14.5 kD upon reduction with 5% β-mercaptoethanol. Depending on the batch of ram rete tesis fluid used, the yield is 32 to 45 ng of 32 kD inhibin per ml of crude RTF processed as determined by amino acid analysis. The purified 32 kD ovine inhibin is 1000 times more potent on a weight basis than crude RTF in the in vitro bioassay. The recovery of FSH-inhibiting activity is about 20% when compared to an internal standard of crude RTF in the in vitro bioassay. Because some of the bioactivity of crude ram RTF may be due to material with truncated α-chain and steroids, it is difficult to assess the true recovery of 32,000 Dalton inhibin from the various chromatographic procedures used. Sequence analysis shows results similar to that of the ovine inhibin purified earlier by conventional chromatography, i.e., the first 24 residues of the N-terminus of the α-chain and the first 29 residues of the N-terminus of the β-chain are closely related but not identical to the α-chain and $β_A$ of porcine inhibin. Although $β_A$ subunits from human, porcine and bovine species are identical to one another, the $β_A$ chain of ovine inhibin has a tyrosine-forphenylalanine substitution at position 17; however, the structure of this hormone has been shown to be highly conserved between species so that an overall length of 116 residues is expected.

The neutralizing effect on inhibin of ovine inhibin-reactive antiserum $Ab_1$ is measured by in vitro assay, which assay is based upon the level of secretion by cultured rat anterior pituitary cells as described in W. Vale et al., *Endocrinology* 91, 562–572 (1972) and G. F. Erickson, et al. *Endocrinology* 103, 1960–1963 (1978). Pituitary cells are enzymatically dispersed and plated into 24-well Linbro tissue culture plates supplied with Dulbecco's modified Eagles medium (DMEM) at about $5 \times 10^5$ cells per well. After washing the cells three times, the cell cultures are incubated in 3 ml DMEM for 2-½ hours at 37° C. with combinations of inhibin (IN) (0.55 ng), normal rabbit serum (NRS) (50 μl) and $Ab_1$ (50 μl). The results show that, whereas inhibin depresses basal level secretions of FSH from pituitary cells, antiserum raised against the conjugate neutralizes the activity of inhibin. Neither NRS nor $Ab_1$ affects the basal level of FSH-secretion, and NRS has no effect on the FSH-releasing inhibition action of inhibin. The suppression of inhibin activity by $Ab_1$ is evidenced by restoration of the amount of FSH released in wells containing both IN and $Ab_1$ as compared to wells containing only IN; this shows that $Ab_1$ binds with and neutralizes ovine inhibin.

Antibodies raised against inhibin are useful in vivo to neutralize the effects of endogenous inhibin. This can be seen by administering the antiserum generated using the synthetic peptide to adult female rats and monitoring the levels of FSH.

The antiserum obtained from the inoculated sheep is diluted 1:1 in 0.05 M sodium carbonate-bicarbonate buffer, pH 9.6, and the diluted antiserum is fed through indwelling venous catheters in the jugular and femoral vein at the rate of 0.2 ml per hour using a Harvard 2265 Multiple Syringe Pump. Infusion is carried out for about 15 hours beginning at 12 noon on the day of proestrus. Blood samples are taken each hour and replaced with an equivalent volume of reconstituted red blood cells.

Monitoring is carried out for 24 hours until 12 noon of estrus, and levels are compared with those of rats which receiving injections of normal rabbit serum(NRS). Whereas the NRS-injected rats show two peaks of plasma FSH values at 4 to 5 PM and at about 12 AM, the rats receiving the antibody show a sustained increase in plasma FSH beginning 3 hours after the start of infusion and remain statistically different, i.e., higher, throughout the rest of the treatment. When the infusion stops after 15 hours, the level of FSH begins a linear decline but remains higher than those rats receiving only NRS injections, showing that these antibodies are effective to neutralize the biological effect of inhibin and thereby increase FSH levels.

Monoclonal antibodies that react with inhibin and thereby suppress its FSH-release-inhibiting activity can likewise be used. Antisera against inhibin may be immortalized by conventional hybridoma-producing protocols. Because polyclonal antisera raised against conjugates are site-specific, i.e., react with those specific portions or sites of the endogenous polypeptide chains that are mimicked by the synthetic peptides, there may be no particular advantage to using monoclonals rather than polyclonals with respect to site-specificity. Nevertheless, monoclonal antibodies do provide a uniformity not provided by polyclonals, and monoclonal antibodies which do not induce undesirable immunological reactions in the species being treated may be preferred for in vivo administration. Furthermore, monoclonal antibody titers may contain less immunologically active extraneous material than antisera raised in inoculated animals.

The generation of inhibin-reactive antisera described hereinbefore is a conventional animal-inoculation procedure; however, it is also possible to induce the production of inhibin-reactive antibodies in vitro by cultured cells, such as by the protocol described by B. Boss, *Brain Research* 291, 193–196 (1984).

As previously set forth, antibodies reactive with inhibin are useful for administering to animals to neutralize the activity of endogenous inhibin and thereby elevate endogenous gonadotropin secretion and exert a profertility effect in human beings and other mammalian animal species having inhibin of a similar structure. Administration of titers of inhibin-reactive antibody increases fertility in female animals and increases spermatogenesis in male animals. To substantially affect secretion levels of gonadotropins in mammalian animals, sufficient antibody should be administered daily to react with and neutralize between about 80 and about 130 nM of inhibin protein per kilogram of body weight. The actual titer of antibody administered depends on the affinity of the particular antibody for inhibin, and in general, between about 20 and about 200 nM of inhibin-reactive antibody is administered daily per kilogram of body weight of a treated animal.

Peptides of the inhibin type may be administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If administration in liquid form is desired, sweetening and/or flavoring may be used, and intravenous administration in isotonic saline, phosphate buffer solutions or the like may be effected.

Inhibin should be administered under the guidance of a veterinarian or a physician, and pharmaceutical compositions will usually contain an effective amount of the peptide in conjunction with a conventional, pharmaceutically-acceptable carrier. The dosage will vary depending upon the specific purpose for which the protein is being administered, and dosage levels in the range of about 0.1 to about 1 milligrams per Kg. of body weight may be used when the protein is administered on a regular basis as a male contraceptive.

Although the method of purification of inhibin has been described primarily in terms of isolation from RTF, inhibin can be similarly purified from other crude extracts, for example follicular fluid. Substantial quantities of inhibin will likely be produced by employing recombinant DNA processes.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed:

1. A substantially pure ovine inhibin protein consisting essentially of greater than 90% by weight of total protein, said inhibin protein consisting of a dimer of a first polypeptide chain having an apparent molecular weight of about 18,000 Daltons, as measured by gel electrophoresis, and a second polypeptide chain having a molecular weight of about 16,500 Daltons, as measured by gel electrophoresis, said first chain being linked to said second chain through disulfide bonding, said dimer, when subjected to reverse phase HPLC elutes from a $C_8$ column of 5 micron particle size and 300 angstrom pore size, at between about 27 and about 28 minutes following the instigation of a straight line gradient flow of Buffers A and B which varies from 25% Buffer B to 90% Buffer B over a period of 45 minutes, at a flow rate of 0.7 ml per minute and a back pressure of about 890 psi, with Buffer A being 0.1% trifluoroacetic acid (TFA) and with Buffer B being 80% acetonitrile in 0.1% TFA:

said first chain having an amino-terminal sequence beginning with Ser-Thr-Pro-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Ala-His-Ala-Asp-Cys-His-Arg -Ala and said second chain having the formula:

H-Gly-Leu-Glu-Cys-Asp-Gly-Lys-Val-Asn-Ile-Cys-Cys-Lys-Lys-Gln-Phe-Tyr-Val-Ser-Phe-Lys-Asp-Ile-Gly-Trp-Asn-Asp-Trp-Ile-Ile-Ala-Pro-Ser-Gly -Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val-Ile-Asn-His-Tyr-Arg-Met-Arg -Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys-Lys-Asp -Ile-Gln-Asn-Met-Ile-Val-Glu-Glu-Cys-Gly-Cys-Ser-OH, said protein specifically inhibiting basal secretion of follicle-stimulating hormone while not inhibiting basal secretion of luteinizing hormone.

2. A protein according to claim 1 having a relative amino acid composition as determined by hydrolysis followed by amino acid analysis in the approximate amounts as follows: Asx 22, Thr 11, Ser 17, Glx 22, Gly 16, Ala 16, Val 11, Met 5, Ile 8, Leu 22, Tyr 8, Phe 10, His 8, Trp 4, Lys 10, Arg 10, Cys 12, and Pro 23.

3. A protein according to claim 1 wherein said first chain is glycosylated.

4. A protein subunit of ovine inhibin having a purity of greater than 90% by weight based upon total protein selected from the group consisting of (a) a first polypeptide having an apparent molecular weight of about 18 kD, as measured by gel electrophoresis, having about 135 amino acid residues, and having an amino terminal sequence beginning with Ser-Thr-Pro-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Ala-His-Ala-Asp-Cys-His-Arg-Ala, and (b) a second polypeptide having an apparent molecular weight of about 16.5 kD, as measured by gel electrophoresis, having the sequence Gly-Leu-Glu-Cys-Asp-Gly-Lys-Val-Asn-Ile-Cys-Cys-Lys-Lys-Gln-Phe-Tyr-Val-Ser-Phe-Lys-Asp-Ile-Gly-Trp-Asn-Asp-Trp-Ile-Ile-Ala-Pro -Ser-Gly-Tyr-His-Ala-Asn-Tyr-Cys-Glu-Gly-Glu-Cys-Pro-Ser-His-Ile-Ala-Gly-Thr-Ser-Gly-Ser-Ser-Leu-Ser-Phe-His-Ser-Thr-Val-Ile-Asn-His-Tyr-Arg -Met-Arg-Gly-His-Ser-Pro-Phe-Ala-Asn-Leu-Lys-Ser-Cys-Cys-Val-Pro-Thr-Lys-Leu-Arg-Pro-Met-Ser-Met-Leu-Tyr-Tyr-Asp-Asp-Gly-Gln-Asn-Ile-Ile-Lys -Lys-Asp-Ile-Gln-Asn-Met-Ile-Val-Glu-Glu-Cys-Gly-Cys-Ser, wherein the first polypeptide is combined through disulfide bonding to the second polypeptide create a dimer which dimer, when subjected to reverse phase HPLC, elutes from a $C_8$ column of 5 micron particle size and 300 angstrom pore size, at between about 27 and about 28 minutes following the instigation of a straight line gradient flow of Buffers A and B which varies from 25% Buffer B to 90% Buffer B over a period of 45 minutes, at a flow rate of 0.7 ml per minute and a back pressure of about 890 psi, with Buffer A being 0.1% trifluoroacetic acid (TFA) and with Buffer B being 80% acetonitrile in 0.1% TFA.

* * * * *

UNITED STATES PATENT AND TRADEMARK OFFICE
CERTIFICATE OF CORRECTION

PATENT NO. : 5,015,729

DATED : May 14, 1991

INVENTOR(S) : Spiess, et al.

It is certified that error appears in the above-identified patent and that said Letters Patent is hereby corrected as shown below:

ABSTRACT: Line 2, change "reta" to --rete--; line 11, change "Leu-Gln" to --Leu-Leu-Gln--; line 13, correct the spelling of --shorter--; line 13 change "by" to --be--.
:Column 1, line 5, change "Contract N01-HD-2-2824 of" to --Grant No. HD-13527 and Contract N01-HD-3-2826 awarded by the National Institutes of Health--.
Column 9, line 60, change "3178-2185" to --3178-3185--.
Column 14, line 22, change "αchains" to --α-chains--.
IN THE CLAIMS: Column 18, line 24, after "electrophoresis," insert --and--; line 36, after "polypeptide" insert --to--; line 36, after "dimer" change "which" to --such--.

Signed and Sealed this

Twenty-sixth Day of January, 1993

Attest:

STEPHEN G. KUNIN

Attesting Officer

Acting Commissioner of Patents and Trademarks